United States Patent
Kuroda et al.

(10) Patent No.: US 6,862,087 B2
(45) Date of Patent: Mar. 1, 2005

(54) RADIATION SOURCE POSITION DETECTION METHOD, RADIATION SOURCE POSITION DETECTION SYSTEM AND RADIATION SOURCE POSITION DETECTION PROBE

(75) Inventors: Yoshikatsu Kuroda, Aichi-ken (JP); Ryouchi Masuko, Tokyo (JP); Tadayuki Takahashi, Kanagawa-ken (JP); Shin Watanabe, Kanagawa-ken (JP)

(73) Assignees: Mitsubishi Heavy Industries, Ltd., Tokyo (JP); Japan Aerospace Exploration Agency, Tokyo (JP)

( * ) Notice: Subject to any disclaimer, the term of this patent is extended or adjusted under 35 U.S.C. 154(b) by 0 days.

(21) Appl. No.: 10/441,024

(22) Filed: May 20, 2003

(65) Prior Publication Data

US 2004/0037394 A1 Feb. 26, 2004

(30) Foreign Application Priority Data

May 20, 2002 (JP) .................................... 2002-145097

(51) Int. Cl.[7] .......................... G01B 11/26; G01T 1/24; G01T 3/00
(52) U.S. Cl. ........................ 356/141.1; 250/370.1; 250/390.12
(58) Field of Search ................ 356/5.01–5.15, 356/141.1; 250/201.6, 390.12, 370.1

(56) References Cited

U.S. PATENT DOCUMENTS

| | | | | |
|---|---|---|---|---|
| 4,047,816 A | * | 9/1977 | Pell et al. | 356/139.03 |
| 4,172,226 A | * | 10/1979 | Rubin | 250/394 |
| 4,964,722 A | * | 10/1990 | Schumacher | 356/139.03 |
| 5,757,478 A | * | 5/1998 | Ma | 356/141.2 |

FOREIGN PATENT DOCUMENTS

| | | |
|---|---|---|
| JP | 7-294652A A | 11/1995 |
| JP | 2003-142670 A | 5/2003 |
| JP | 2003-315465 A | 11/2003 |

OTHER PUBLICATIONS

Online Space Notes/Artificial Satellites, "ISAS's Radiotelescope Satellite 'Halca'," http://spaceboy.nasdda.go.jp, (with English translation/version).

* cited by examiner

*Primary Examiner*—Bernarr E. Gregory
*Assistant Examiner*—Brian Andrea
(74) *Attorney, Agent, or Firm*—Birch, Stewart, Kolasch & Birch, LLP

(57) ABSTRACT

A radiation source position detection system is provided, wherein three radiation detectors are arranged at different positions. Based on radiations incident to each of the radiation detectors, curved surfaces where a radiation source exists are calculated. By solving equations of each of the curved surfaces simultaneously, the position of the radiation source is detected.

16 Claims, 6 Drawing Sheets

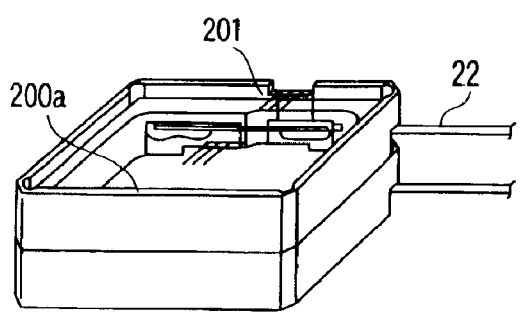
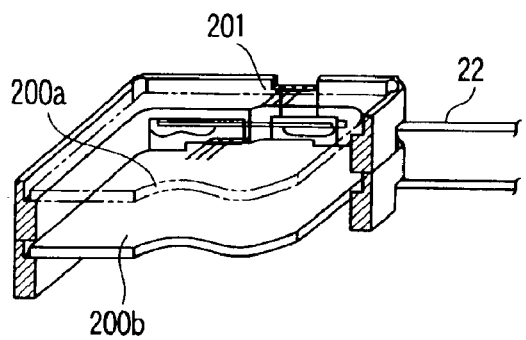
FIG. 2A  FIG. 2B
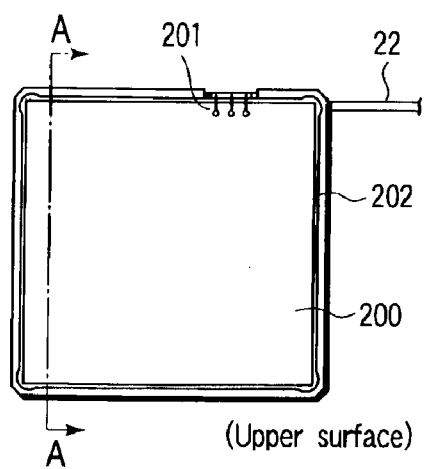
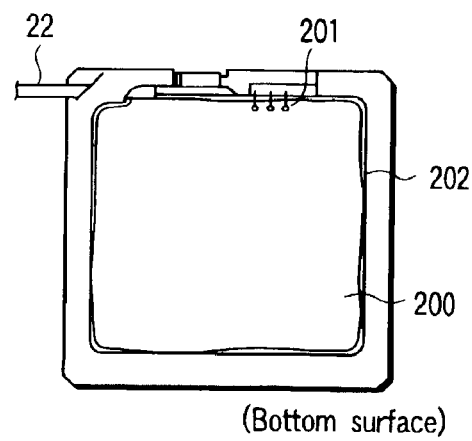
(Upper surface)  (Bottom surface)
FIG. 3A  FIG. 3B
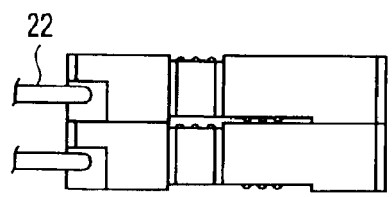
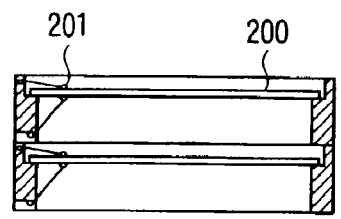
FIG. 3C  FIG. 3D

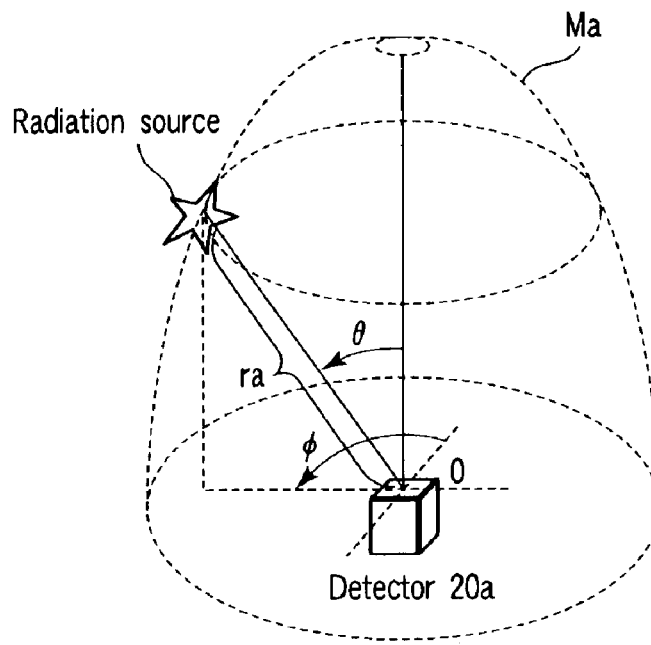
F I G. 4A
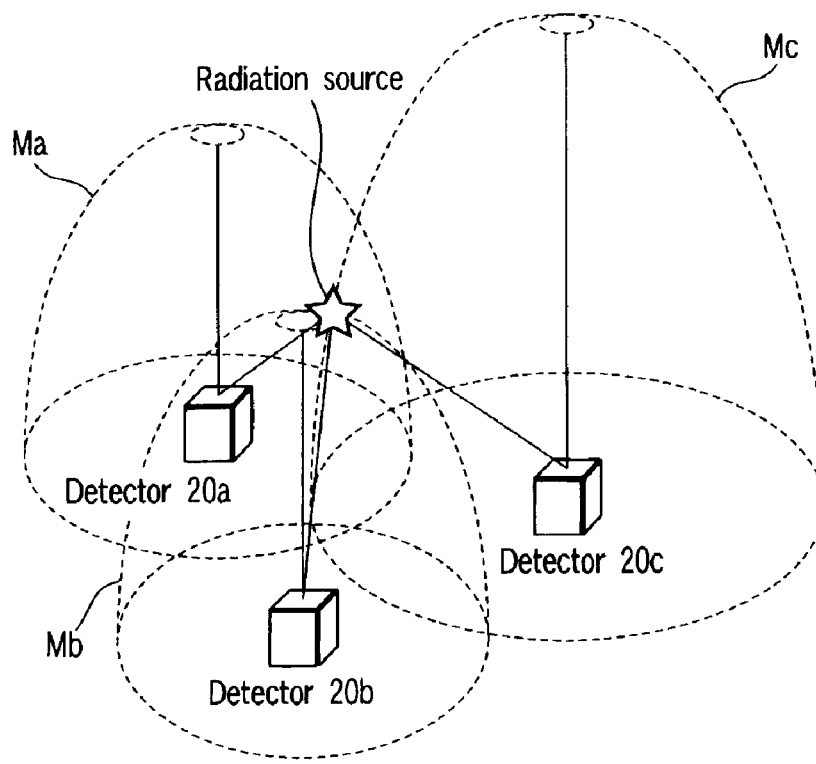
F I G. 4B

RADIATION SOURCE POSITION DETECTION METHOD, RADIATION SOURCE POSITION DETECTION SYSTEM AND RADIATION SOURCE POSITION DETECTION PROBE

CROSS-REFERENCE TO RELATED APPLICATIONS

This application is based upon and claims the benefit of priority from the prior Japanese Patent Application No. 2002-145097, filed May 20, 2002, the entire contents of which are incorporated herein by reference.

BACKGROUND OF THE INVENTION

1. Field of the Invention

The present invention relates to a radiation source position detection method, a radiation source position detection system, and a radiation source position detection probe for use in detecting a position of a radiation source in such fields as nuclear power development and medicine.

2. Description of the Related Art

A radiation detection system for detecting radiation such as hard X-rays or γ-rays and generating image information finds application in various technological fields. The physical condition and the spatial structure of a given heavenly body can be known, for example, by detecting the radiation field from the particular heavenly body. Also, a tomographic image of a human body or the like can be acquired by radiating the X-rays on the human body or the like and checking the transmitted waves. Various other applications include nuclear power (glass solidification testing and radiation monitoring devices for radiation waste, etc.), nondestructive inspection (semiconductor inspection device, etc.) and resource exploration (survey of underground resources, etc.).

Most of the conventional radiation detection systems, however, detect the photons flying to the surface of the detector, and the energy of the radiation is measured or imaged based on the detected photons. The position of the radiation source, therefore, cannot be detected with high accuracy.

SUMMARY OF THE INVENTION

The present invention has been developed in view of the situation described above, and an object thereof is to provide a radiation source position detection method, a radiation source position detection system and a radiation source position detection probe for detecting a position of a radiation source with a high accuracy.

In order to achieve this object, the present invention employs various means described below.

According to a first aspect of the invention, there is provided a method of detecting a radiation source position, which comprises: detecting a radiation from a radiation source at three or more different detection positions; estimating at least three curved surfaces where the radiation source exists, based on the radiation detected at each of the detection positions; and acquiring the position of the radiation source based on the each estimated curved surface.

According to a second aspect of the invention, there is provided a method of detecting a radiation source position, which comprises: detecting a radiation from a radiation source at three or more different detection positions; estimating at least three curved surfaces where the radiation source exists, based on the radiation detected along each incident direction; and acquiring the position of the radiation source based on the each estimated curved surface.

According to a third aspect of the invention, there is provided a radiation source position detection system, which comprises: at least three radiation detectors which are arranged at different positions and detect the incident radiations, respectively; estimation units which estimate a curved surface where the radiation source exists, based on the radiation detected by the each radiation detector; and position acquisition units which detect the position of the radiation source, based on each curved surface estimated by each of the estimation units.

According to a fourth aspect of the invention, there is provided a radiation source position detection system comprising: radiation detectors which detects an incident radiation along different first, second, and third directions, respectively; estimation units which estimate a first curved surface, a second curved surface, and a third curved surface where the radiation source exists, based on each radiation detected along the first, second and third directions, respectively; and position acquisition units which acquire the position of the radiation source based on each of the curved surfaces estimated by each of the estimation units.

According to a fifth aspect of the invention, there is provided a radiation detection probe for detecting incident radiations along different first, second, and third directions, which comprises: a first layer having a first detection plate; and a second layer arranged in a predetermined spaced relation in a front or subsequent stages of the first layer and having second, third, and fourth detection plates, wherein the incident radiations are detected along the first direction by a first detection unit including the first detection plate and the second detection plate, along the second direction by a second detection unit comprising the first detection plate and the third detection plate, and along the third direction by a third detection unit comprising the first detection plate and the fourth detection plate, respectively.

BRIEF DESCRIPTION OF DRAWINGS

FIG. 2A as an external view of a radiation detector 20a, etc., and FIG. 2B a view for explaining an internal configuration of the radiation detector 20a, etc;

FIG. 3A is a top plan view, FIG. 3B a bottom view, FIG. 3C a rear view, and FIG. 3D a sectional view taken along line A—A in FIG. 3A of the radiation detector 20a, etc;

FIGS. 4A and 4B are diagrams for explaining the concept of position measurement carried out by the radiation source position measuring system 10;

DETAILED DESCRIPTION OF THE INVENTION

Figure 1:
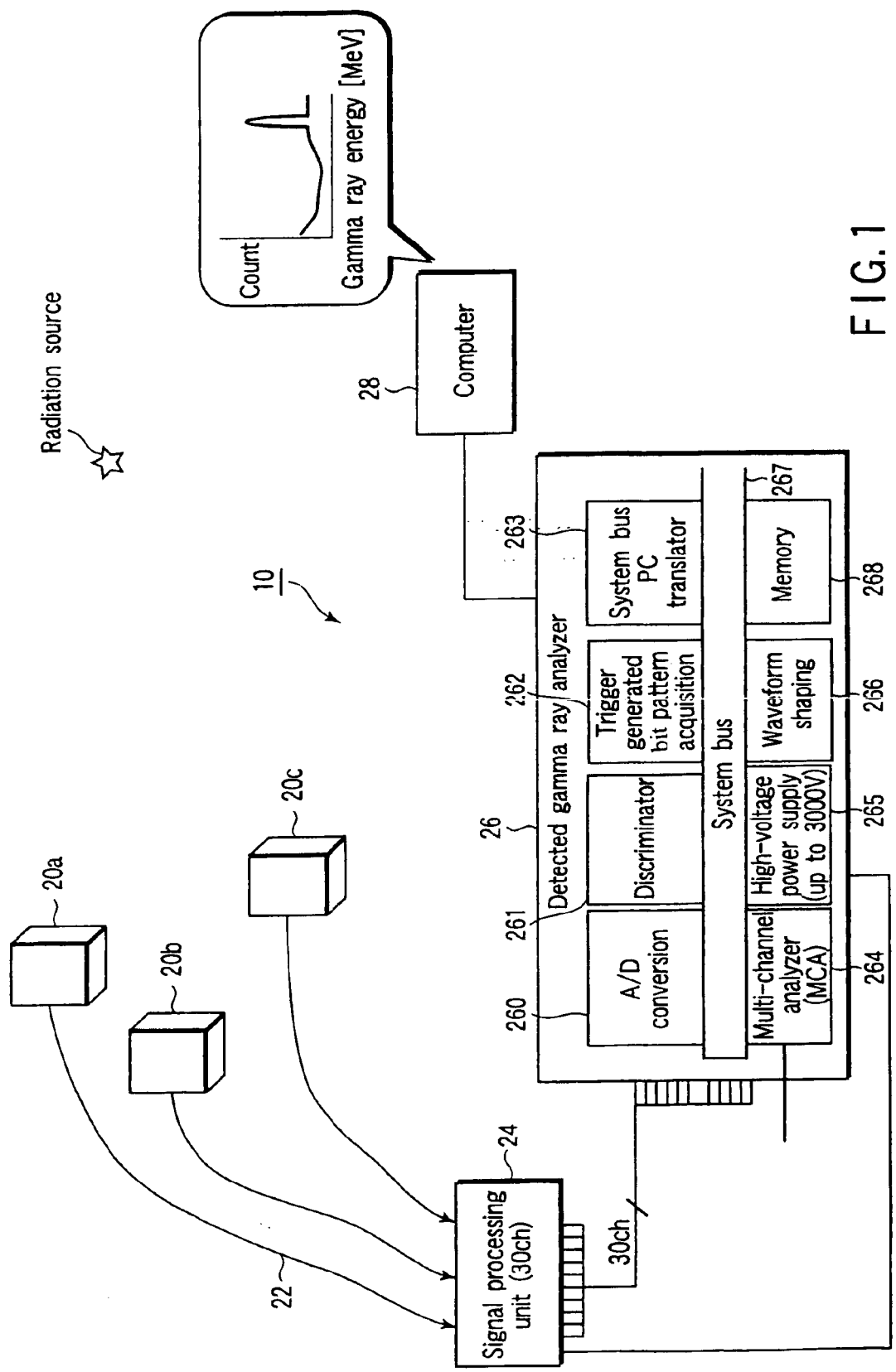
FIG. 1 is a diagram showing a radiation source position measuring system 10 according to an embodiment of the invention.

First and second embodiments of the invention will be explained below with reference to the accompanying drawings. In the description that follows, the component parts having substantially the same function and configuration will be designated by the same reference numeral and will be explained again only when necessary.

(First Embodiment)

FIG. 1 is a diagram showing a radiation source position measuring system 10 according to the first embodiment of the invention. The radiation source position measuring system 10 finds practical applications in such fields as observation of heavenly bodies, nuclear power development, nondestructive inspection, and survey of resources. As shown in FIG. 1, the radiation source position measuring system 10 comprises radiation detectors 20a, 20b, 20c, a signal processing unit 24, a detected gamma ray analyzer 26 and a computer 28.

The radiation detectors 20a, 20b, 20c each detect the radiation such as the X-rays or γ-rays. The radiation detectors 20, as described later, each have a structure in which at least two detection plates are stacked as a detection surface along the direction of incidence of the radiation. Each detection plate is independently movable along the direction of incidence of the radiation. The system constituted the radiation detectors 20 and the predetermined signal processing system has a function as a laser range finder which detects the distance to the radiation source.

The signal processing unit 24 amplifies a detection signal detected by each of the radiation detectors 20a, 20b, 20c and prevents a noise from being mixed or the S/N from being reduced. Also, the signal processing unit 24 performs the signal processing such as the sampling of the detection signal, further amplification thereof, generation of a trigger signal and sample holding.

The detected gamma ray analyzer 26 includes an A/D converter 260, a discriminator 261, a trigger signal generation bit pattern acquisition unit 262, a system bus PC translator 263, a MCA (multichannel analyzer) 264, a high voltage power supply 265, a waveform shaping unit 266, a system bus 267, and a memory 268.

The A/D converter 260 converts an input analog signal into a digital signal.

The discriminator 261 retrieves the original signal wave from the signal wave subjected to frequency modulation or phase modulation.

The trigger signal generation bit pattern acquisition unit 262 acquires a bit pattern of the detected gamma ray based on the signal wave extracted by the discriminator 261. The gamma ray detection information acquired by the trigger signal generation bit pattern acquisition unit 262 is transmitted to the computer 28 to measure the distance and direction to a gamma ray source described later. The trigger signal generation bit pattern may alternatively be adapted to be acquired by the computer 28.

The system bus PC translator 263 is a transmitter for transmitting various signals to the computer 28 from the system bus 267.

The MCA (multichannel analyzer) 264 processes into a histogram signal values of the digital signal converted by the A/D converter 260.

The high voltage power supply 265 generates a high voltage to be applied to the electrode of each detection plate of the radiation detectors 20a, 20b, 20c. Each detection plate, which has the electrode thereof supplied with a voltage from the high voltage power supply 265, may be a semiconductor, in which case it generates electrons and holes upon receipt of the gamma ray. In the case where the detection plate is a scintillator, on the other hand, the gamma ray enters it thereby to generate wide areas light from visible light to ultraviolet light.

The waveform shaping unit 266 converts the waveform of an input pulse into a predetermined waveform along the amplitude axis or time axis.

The system bus 267 is a circuit for transmitting or receiving various signals to or from the devices in the detected gamma ray analyzer 26.

The memory 268 stores a bit pattern of the gamma ray acquired through the trigger signal generation bit pattern acquisition unit 262.

The computer 28 is a work station or a personal computer having the functions of arithmetic processing, image processing, etc. The computer 28 measures the energy count distribution of the detected gamma ray as shown in FIG. 1, calculates the area described later where the gamma ray source exists, and detects the position of the gamma ray source, based on the gamma ray detection information of the radiation detectors 20a, 20b, 20c received from the detected gamma ray analyzer 26.

The detected gamma ray analyzer 26 may be equipped with an additional function of arithmetic processing, image processing, etc. so as to carry out the calculation of the area described later where the gamma ray source exists, the detection of the gamma ray source position, etc.

(Radiation Detector)

Next, a general configuration of the radiation detectors 20a, 20b, 20c (hereinafter referred to as the radiation detector 20a, etc.) will be explained in detail.

FIG. 2A is an outside view of the radiation detector 20a, etc., and FIG. 2B is a view for explaining the internal configuration of the radiation detector 20a, etc. FIG. 3A is a top plan view, FIG. 3B a bottom view, FIG. 3C a rear view, and FIG. 3D a sectional view taken along line A—A in FIG. 3A, showing the radiation detector 20a, etc.

As shown in FIGS. 2A, 2B, and 3A–3D, the radiation detector 20a, etc. includes two detection plates 200 each having a first electrode 201 and a second electrode 202 for collecting the charge generated when the radiation enters each of the detection plates 200. One of the first and second electrodes is assigned to the anode and the other is assigned to the cathode.

The detection plates 200 are each a semiconductor plate composed of a semiconductor such as CdTe, CdZnTe, Si, Ge, etc. A material such as scintillator (NaI, CsI, GSO, BGO, etc., for example) other than the semiconductor can also be used. Especially in the case where the detection plate 200 is configured of a semiconductor detector, a potential can be applied to each plate individually by the first electrode 201 and the second electrode 202.

The detection plates 200 are composed of a semiconductor or the like having a flat surface to assure an improved shield factor and simplify the configuration of the system as shown in FIGS. 2A, 2B, and 3A–3D. This configuration makes it possible to count the number of incident gamma rays with high accuracy and detect the energy thereof (spectrum analysis) Nevertheless, the detection plates 200 are not limited to the flat surface (plane surface) shown in FIGS. 2A, 2B, and 3A–3D, but may take a form capable of acquiring an image as described in Japanese Patent Application No. 2001-339711. Furthermore, when the detection plates 200 are scintillator plates, optical signal acquisition system is needed instead of the electrodes 201, 202.

The radiation detectors 20 and the detected gamma ray analyzer 26 are connected to each other by connectors 22.

The charge collected by the electrodes is transmitted to the detected gamma ray analyzer 26 in a subsequent stage for each detection plate 200 (channel) (FIG. 3C).

Although the radiation detector 20a, etc., having two detection plates 20 is illustrated in FIGS. 2A, 2B, and 3A–3D, more detection plates 200 may be included to improve the detection accuracy or increase the degree of freedom of detection techniques. In any configuration, the distance between the detection plates 200 is preferably controllable.

The radiation detector 20a, etc., has a charge collection mechanism for each detection plate 200. Therefore, the position where the gamma ray reacts (i.e., the detection plate 200 at which the gamma ray reacts) and the energy detected there can be known independently of each other. Also, it is possible to know the distance to the radiation source.

Specifically, with the detectors 20, the energy distribution of the incident gamma rays or the energy value of the line gamma rays can be known from the energy spectrum of the gamma rays detected by each detection plate 200 or the total sum thereof. Also, gamma rays (line gamma rays) having a single energy are generally required to measure the distance to the radiation source. In measuring the distance to the radiation source with the detectors 20, only the phenomenon in which the energy equal to that of the incident gamma rays is detected by any plate 200 (only one layer) is selected, and the number of the phenomena thus detected is compared between the plates 200. This comparison makes it possible to know the distance of the line gamma ray from the detectors.

(Measurement of Gamma Ray Source Distance)

First, an explanation will be given of the position measuring process using the radiation source position measuring system 10 described above. FIGS. 4A and 4B are diagrams for explaining the position measuring process executed by the radiation source position measuring system 10. In the polar coordinate system shown in FIG. 4A, assume that the radiation source is located at the position indicated by (r, θ, φ). Then, according to the method described in Japanese Patent Application No. 2002-122524, the radiation count $C_i$ at the i-th detection plate from the plane of incidence is proportional to the following equation (1):

$$A_i(r, \theta) \cdot r^2/[r^2 \sin^2\theta + \{r \cos\theta + (i-1)d\}^2] \quad (1)$$

where $A_i(r, \theta)$ represents the effect of radiation absorption by the detection plate in the front stage, which is dependent on the shape of the detectors (i.e., the shape of the detection plates). Also, $r^2/[r^2 \sin^2\theta + \{r \cos\theta + (i-1)d\}^2]$ indicates the effect of the distance to the radiation source varied from one detection plate to other.

Based on this equation (1), the ratio of the count between the detection plates of the detector 20a is measured, for example, and the value Ga (ra, θa)=0 associated with the minimum value of $\chi^2$ can be obtained by $\chi^2$ fitting. This is also the case with the other detectors 20b, 20c, and as shown in FIG. 4B, the equations Gb (rb, θb)=0, Gc (rc, θc)=0 of curved surfaces minimizing the value of $\chi^2$ can be obtained based on the detection data of the radiation detectors 20b, 20c, respectively.

The curved surfaces Ga (ra, θa)=0, Gb (rb, θb)=0, Gc (rc, θc)=0 thus obtained, on which the radiation source is estimated to exist, can be rewritten as Ma (r, θ, φ)=0, Mb (r, θ, φ)=0, Mc (r, θ, φ)=0, respectively, by coordinate transformation. In the radiation source position measuring system 10 according to this embodiment, the position of the radiation source is uniquely determined by simultaneously solving the equations of the curved surfaces Ma, Mb, Mc determined in the above-mentioned way. This can be intuitively explained as follows. Specifically, the radiation source is located on the curved surfaces Ma, Mb, Mc, for example, on the curve where the curved surface Ma and the curved surface Mb cross each other. Assuming that this curve is C, the crossing point between the curve C and the curved surface Mc is the solution of the simultaneous equations described above, which indicates the coordinate (r, θ, φ) of the radiation source.

The curved surfaces Ga (ra, θa)=0, Gb (rb, θb)=0, Gc (rc, θc)=0 on which the radiation source is estimated to exist can be determined also by the method of numerical calculation described below or the method using a calibration test as well as by the analysis method described above.

The method using the numerical calculation is described below. Specifically, the ratio of the count for the detection plates obtained with the radiation source arranged at a given position is stored by being determined in advance by simulation using, for example, Monte Carlo analysis. At the same time, the information such as the shape of the detectors 20 (i.e., the shape of the detection plates 200) is also desirably stored.

Next, the ratio of the count obtained by simulation is stored by being determined for each position in a predetermined area (for example in an area where the radiation source is considered to exist).

The radiation is detected actually by each detector 20. Based on each detection result, the ratio of the count for each detection plate is determined by the above-mentioned method, and by comparing it with the simulation result, a candidate radiation source position is selected for each detector.

The candidate radiation source position thus determined should exist on the curved surfaces Ga (ra, θa)=0, Gb (rb, θb)=0, Gc (rc, θc)=0 where the radiation source is estimated to exist. Based on the candidate radiation source position, therefore, the curved surfaces Ga (ra, θa)=0, Gb (rb, θb)=0, Gc (rc, θc)=0 can be determined for each detector.

In the method based on the calibration test, on the other hand, the relation between the ratio of the count for each detection plate and the detector position is determined in advance by actual measurement instead of using the simulation. Based on this relation, a candidate radiation source position is selected from the actual detection result, so that the curved surfaces Ga (ra, θa)=0, Gb (rb, θb)=0, Gc (rc, θc)=0 can be determined for each detector.

As described above, in the system 10, at least three equations of a curved surface where the radiation source exists are specified by at least three radiation detectors according to the analysis method, the numerical calculation method or the calibration test, and these three equations of curved surfaces are simultaneously resolved. In this way, the spatial position of the radiation source can be accurately determined. As a result, the operator can easily specifying the position of the radiation source by arranging and detecting the radiation detectors, for example, at three different positions.

(Second Embodiment)

Figure 5:
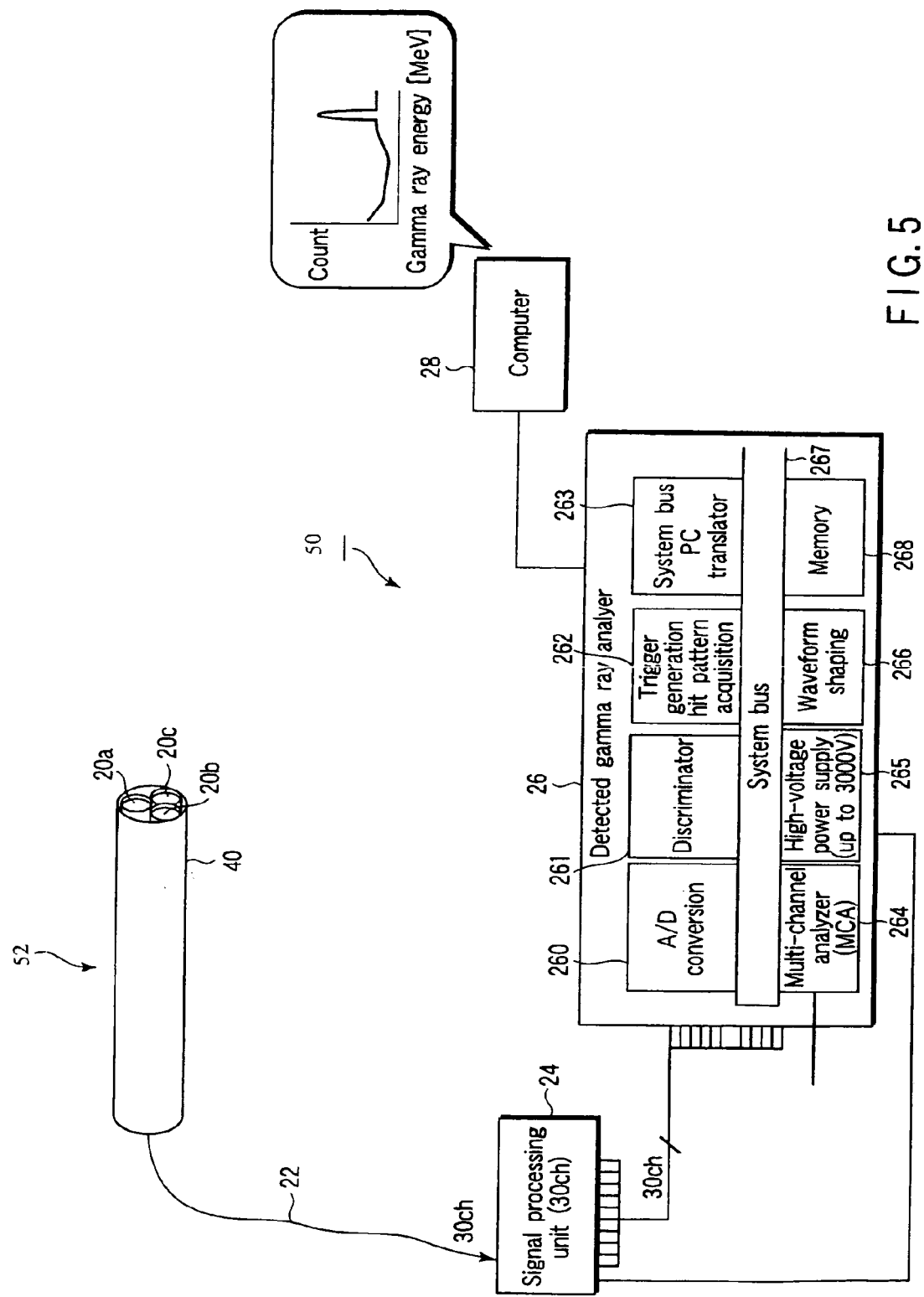
FIG. 5 is a diagram showing a general configuration of a radiation source position measuring system 50 according to an embodiment of the invention.

A radiation source position measuring system according to a second embodiment finds practical applications in the medical field, for example. FIG. 5 is a diagram showing a general configuration of a radiation source position measuring system 50 according to this embodiment. The radiation source position measuring system 50 includes radiation detectors 20a, 20b, 20c of a smaller size, which are stored in a single housing 40 to configure a probe 52. The other component parts are substantially identical to the corresponding ones of the system 10 shown in FIG. 1.

Figure 6:
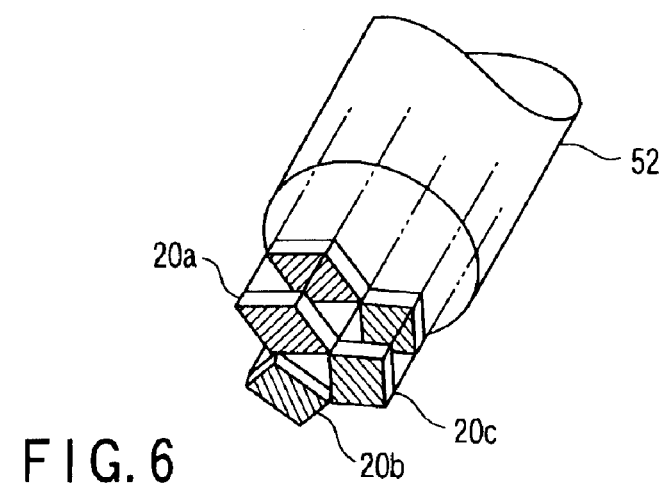
FIG. 6 is a view for explaining a configuration of a probe 52.
Figure 7A:
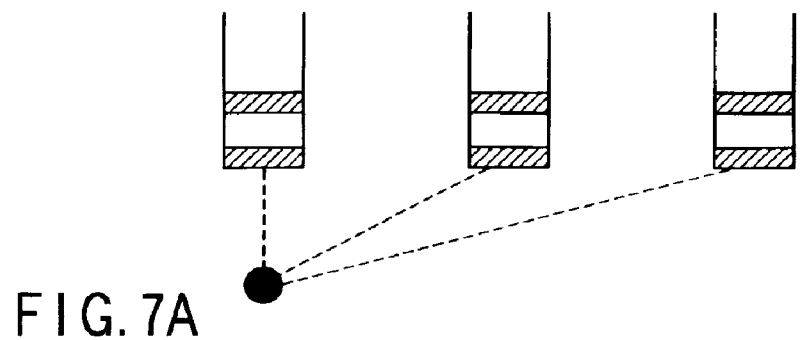
FIGS. 7A to 7C are views for explaining the relative positions of the radiation detectors.
Figure 7B:
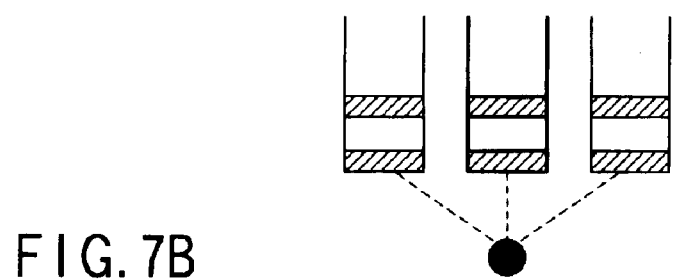
Figure 7C:
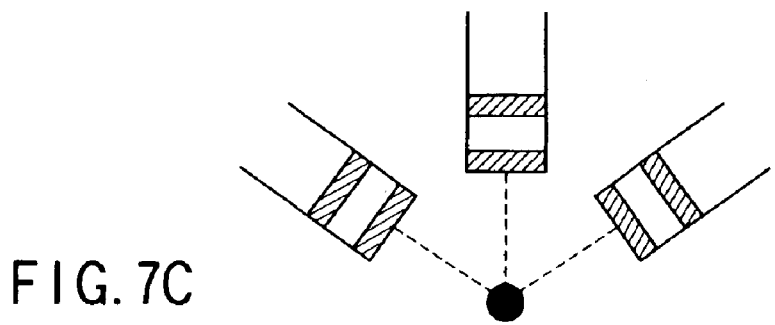

FIG. 6 is a view for explaining a configuration of the probe 52. As shown in FIG. 6, the probe 52 has small-sized radiation detectors 20a, 20b, 20c. The relative positions of the radiation detectors are not specifically limited but must be such that the radiation source can be determined uniquely by the above-mentioned method. Specifically, any relative positions will do as far as the equations of the curved surfaces Ma, Mb, Mc are independent of each other. For example, the radiation detectors may be arranged in spaced relation with each other as shown in FIG. 7A, or may be arranged adjacently to each other as shown in FIG. 7B. Also, as shown in FIG. 7C, a given detection plate 200 is not necessarily parallel to the detection plates 200 configuring the other radiation detectors. Nevertheless, in order to assure the compactness of the probe 52, it is preferable to arrange the radiation detectors 20a, 20b, 20c in parallel to each other with a small distance therebetween.

An example of improper relative positions of the radiation detectors 20a, 20b, 20c is an arrangement on the same axis. This arrangement makes it impossible to uniquely determine the resolution of simultaneous equations for the curved surfaces Ma, Mb, Mc as a position of the radiation source.

According to the above-mentioned method, the position of the radiation source can be determined by solving the simultaneous equations as far as the three independent curved surfaces (i.e. Ma, Mb, Mc shown in FIG. 4B) where the radiation source exists. It is therefore crucial for the system that at least three independent curved surfaces where the radiation source exists can be specified. In other words, any configuration can be employed as long as independent three curved surfaces can be specified.

From this viewpoint, modifications of the probe 52 will be explained below.

FIGS. 8A, 8B, 9A, 9B, 10A, and 10B are views for explaining modifications of the probe 52. The probe 52 shown in FIG. 8A includes a first detection layer 53 fitted with a single small-sized detection plate 200 and a second detection layer 54 fitted with three small-sized detection plates 200. Even with this configuration of the probe 52, as shown in FIG. 82, three independent detectors A, B, C having the detection plate 200 in the front stage and the detection plate 200 in the subsequent stage can be configured. Thus, three independent curved surfaces can be specified.

Figure 8A:
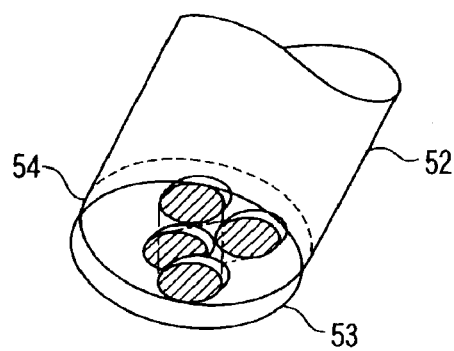
FIGS. 8A and 8B are views for explaining the probe 52 according to a modification of the invention.
Figure 8B:
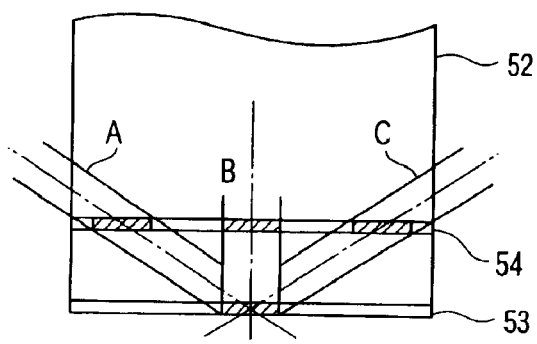
Figure 9A:
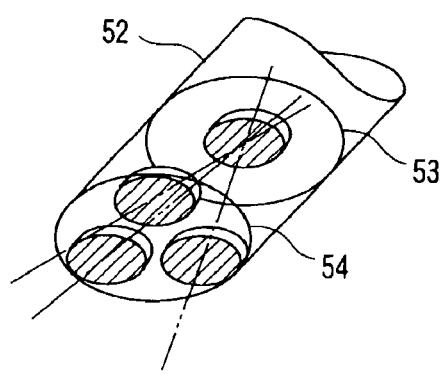
FIGS. 9A and 9B are views for explaining the probe 52 according to a modification of the invention.
Figure 9B:
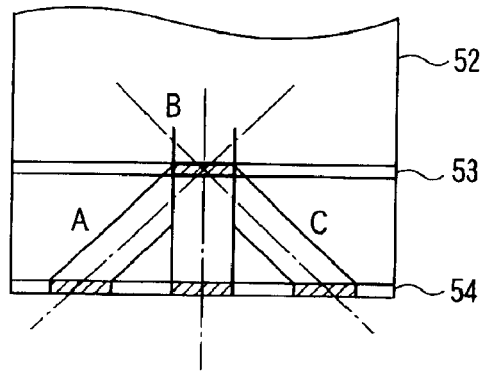

In the probe 52 shown in FIG. 9A, on the other hand, the first detection layer 53 and the second detection layer 54 of the detection plate 200 shown in FIG. 8B are replaced with each other. Even with this configuration of the probe 52, as shown in FIG. 9B, three independent detectors A, B, C including the detection plate 200 in the front stage and the detection plate 200 in the subsequent stage can be configured. Thus, three independent curved surfaces can be specified.

Figure 10A:
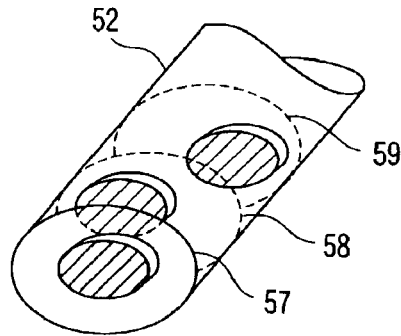
FIGS. 10A and 10B are views for explaining the probe 52 according to a modification of the invention.
Figure 10B:
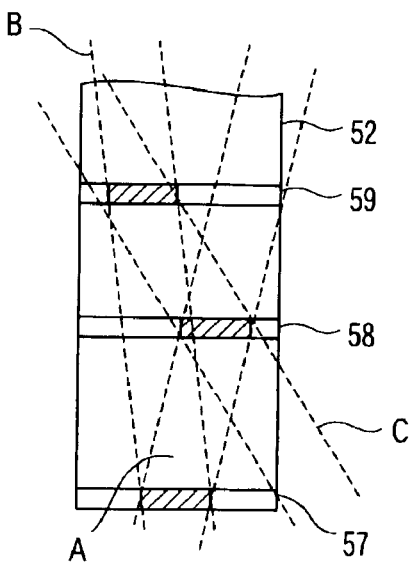

In the probe 52 shown in FIG. 10A, first detection layers 57, 58, 59 each fitted with a single small-sized detection plate 200 are aligned in the same direction. At least one detection plate of the first detection plate of the first detection layers 57, 58, 59, however, fails to share the center axis with the other detection plates or has a different shape or size from the remaining detection plates. Even with this configuration of the probe 52, as shown in FIG. 10B, three independent detectors A, B, C with the detection plates 200 differently combined can be configured. Thus, three independent curved surfaces can be specified.

With the above-mentioned configuration, the portions that have absorbed a chemical marked by a radioactive isotope, for example, in the radiation medical field can be specified with high accuracy. Especially, the above-mentioned probe is so compact that it can be placed adjacently to a deceased part by hand or inserted into a narrow part or otherwise can be arranged easily at the desired position.

Embodiments of the present invention are described above. Various modifications and alterations can be conceived by those skilled in the art within the scope and spirit of the invention, and such modifications and alterations are understood to be covered by the scope of the invention. As shown in (1) and (2) below, for example, the invention is variously modifiable without departing from the scope thereof.

(1) According to the first and second embodiments, the curved surfaces Ma, Mb, Mc having a radiation source are specified at three different positions by the three radiation detectors 20a, 20b, 20c. In contrast, the curved surfaces Ma, Mb, Mc where the radiation source exists at three different positions may alternatively be specified by a configuration in which a single radiation detector 20a is used with the detection position thereof being displaced.

(2) From the viewpoint of prevention of exposure and an improved operability, a mechanism may be added to control the position of the radiation detector 20a, etc. remotely.

Also, the embodiments can be appropriately combined as far as possible, in which case a combined effect can be achieved. Further, the embodiments described above contain various stages of the invention, and therefore various inventions can be extracted by an appropriate combination of a plurality of the disclosed component elements. Even in the case where some component elements are deleted from all the component elements disclosed in the embodiments, for example, the problem described in BRIEF SUMMARY OF THE INVENTION can be solved. In the case where at least one of the effects described in the specification can be obtained, the configuration with some component elements deleted can be extracted as an invention.

What is claimed is:

1. A method of detecting a radiation source position, comprising:
   detecting a radiation from a radiation source at three or more different detection positions with a detector which includes a plurality of detection plates arranged in predetermined space relations respectively;
   estimating at least three curved surfaces where the radiation source exists by calculating a function to minimize a value of chi-square with respect to each of the detection position respectively, the value of chi-square using each of the number of radiations incident to each detection plates and each of the predetermined space relations; and
   acquiring the position of the radiation source based on said each estimated curved surface.

2. A method of detecting a radiation source position according to claim 1,
   wherein the position of the radiation source is acquired by an analysis method in which equations of the at least three curved surfaces are simultaneously solved, a method of numeral calculation in which ratio of count for each of the detection plates with the radiation source arranged at a plurality of given positions is determined by simulation and a method based on a calibration test in which a relation between ratio count for each of the detection plates with the radiation source arranged at a plurality to given positions is determined by actual measurement.

3. A method of detecting a radiation source position, comprising:

detecting a radiation from a radiation source at three or more different detection positions with a detector which includes a plurality of detection plates arranged in predetermined space relations respectively;

estimating at least three curved surfaces where the radiation source exists by calculating a function to minimize a value of chi-square with respect to at least different three directions respectively, the value of chi-square using each of the number of radiations incident to each detection plates and each of the predetermined space relations; and acquiring the position of the radiation source based on said each estimated curved surface.

4. A method of detecting a radiation source position according to claim 3, wherein the position of the radiation source is acquired by an analysis method in which equations of the at least three curved surfaces are simultaneously solved, a method of numerical calculation in which ratio of count for each of the detection plates with the radiation source arranged at a plurality to given positions is determined by simulation, and a method based on a calibration test in which a relation between ratio count for each of the detection plates with the radiation source arranged at a plurality to given positions is determined by actual measurement.

5. A radiation source position detection system comprising:

at least three radiation detectors each of which includes a plurality of detection plates arranged in predetermined space relations respectively and detects incident radiations b each detection plate;

an estimation unit which estimates at least three curved surfaces where the radiation source exists by calculating a function to minimize a value of chi-square with respect to each of the detection position, the value of chi-square using each of the number of radiations incident to each detection plates and each of the predetermined space relations; and position acquisition units which acquires the position of the radiation source based on said each estimated curved surfaces.

6. A radiation source position detection system according to claim 5, wherein the position of the radiation source is acquired by an analysis method in which equations of the at least three curved surfaces are simultaneously solved, a method of numeral calculation in which ratio of count for each of the detection plates with the radiation source arranged at a plurality to given positions is determined by simulation, and a method based on a calibration test in which a relation between ratio count for each of the detection plates with the radiation source arranged at a plurality to given positions is determined by actual measurement.

7. A radiation source position detection system according to claim 6, wherein said each detection plate is composed of a semiconductor or a scintillator.

8. A radiation source position detection system comprising:

radiation detectors which detects an incident radiation along different first, second and third directions, respectively;

estimation unit which estimate a first curved surface, a second curved surface, and a third curved surface where the radiation source exists, by calculating a function to minimize a value of chi-square with respect to first, second, and third directions respectively, the value or chi-square using each of the number of radiations incident to each detection plates and each of the predetermined relations; and position acquisition units which acquire the position of the radiation source based on each of the curved surfaces estimated by each of the estimation unit.

9. A radiation source position detection system according to claim 8;

wherein the radiation detectors each includes a first layer having a first detection plate; and a second layer arranged in predetermined spaced relation in a front or subsequent stage of the first layer and having second, third and fourth detection plates, the radiation incident from the first direction is detected by a first detection unit including the first detection plate and the second detection plate, the radiation incident from the second direction is detected by a second detection unit including the first detection plate and the third detection plate, and the radiation incident from the third direction is detected by a third detection unit including the first detection plate and the fourth detection plate, and said each estimation unit detects the number of radiations incident to each detection plate; estimates the first curved surface where the radiation source exists, based on the number of the radiations incident to said each detection plate configuring the first detection unit and the distance between the first detection plate and the second detection plate; estimates the second curved surface where the radiation source exists, based on the number of the radiations incident to said each detection plate configuring the second detection unit and the distance between the first detection plate and the third detection plate; and estimates the third curved surface where the radiation source exists, based on the number of the radiations incident to said each detection plate configuring the third detection unit and the distance between the first detection plate and the fourth detection plate.

10. A radiation source position detection system according to claim 9, wherein each of the first to fourth detection plates includes a semiconductor or a scintillator.

11. A radiation source position detection system according to claim 8;

wherein the radiation detectors each includes:

a first detection plate; a second detection plate arranged in a first spaced relation with the first detection; and a third detection plate arranged in a second spaced relation with the first detection plate and having a center axis different from that of the first detection plate and the second detection plate, the radiation ray incident from the first direction is detected by a first detection unit including the first detection plate and the second detection plate, the radiation ray incident from the second direction is detected by a second detection unit including the first detection plate and the third detection plate, and the radiation ray incident from the third direction is detected by a third detection unit including the second detection plate and the third detection plate, and said estimation unit detects the number of radiations incident to each detection plate; estimates the first curved surface where the radiation source exists, based on the number of the radiations incident to said each detection plate configuring the first detection unit and the distance between the first detection plate and the second detection plate; estimates the second curved surface where the radiation source exists, based on the number of the radiations incident to said each detection plate configuring the second detection unit and the distance between the first detection plate and the third detection plate; and estimates the third curved surface where the radiation source exists, based on the number of the radiations incident to said each detection plate configuring the third detection unit and the distance between the second detection plate and the third detection plate.

12. A radiation source position detection system according to claim 11, wherein each of the first to third detection plates includes a semiconductor or scintillator.

13. A radiation detection probe for detecting incident radiations along different first, second and third directions, comprising:
- a first layer having a first detection plate; and
- a second layer arranged in a predetermined spaced relation in a front or subsequent stages of the first layer and having second, third and fourth detection plates,
- wherein the incident radiations are detected along the first direction by a first detection unit including the first detection plate and the second detection plate, along the second direction by a second detection unit including the first detection plate and the third detection plate, and along the third direction by a third detection unit including the first detection plate and the fourth detection plate, respectively.

14. A radiation detection probe according to claim 13, wherein each of the first to fourth detection plates includes a semiconductor or a scintillator.

15. A radiation detection probe for detecting incident radiations along different first, second and third directions, comprising:
- a first detection plate;
- a second detection plate arranged in a first spaced relation with the first detection plate; and
- a third detection plate arranged in a second spaced relation with the first detection plate and having a shape or a center axis different from that of the first detection plate and the second detection plate,
- wherein the incident radiations are detected along the first direction by a first detection unit including the first detection plate and the second detection plate, along the second direction by a second detection unit including the first detection plate and the third detection plate, and along the third direction by a third detection unit including the second detection plate and the third detection plate, respectively.

16. A radiation source position detection probe according to claim 15, wherein each of the first to third detection plates includes a semiconductor and a scintillator.

* * * * *